United States Patent [19]

Yamamoto et al.

[11] Patent Number: 5,565,425
[45] Date of Patent: Oct. 15, 1996

[54] VIRAL INFECTION AND PROLIFERATION INHIBITORS

[75] Inventors: Naoki Yamamoto; Hideki Nakashima, both of Tokyo; Wataru Motsuchi, Sagamihara; Shigeaki Tanaka, Ayase; Shun'ichi Dosako, Urawa; Yoshihiro Kawasaki; Toshiaki Uchida, both of Kawagoe, all of Japan

[73] Assignee: Snow Brand Milk Products Co., Ltd, Japan

[21] Appl. No.: 204,487

[22] Filed: Mar. 2, 1994

[30] Foreign Application Priority Data

Mar. 4, 1993 [JP] Japan .................. 5-069210

[51] Int. Cl.$^6$ .................. A61K 38/00
[52] U.S. Cl. .................. 514/12; 514/13
[58] Field of Search .................. 514/12, 13

[56] References Cited

U.S. PATENT DOCUMENTS 5,304,633   4/1994   Tomita et al. .................. 530/326

FOREIGN PATENT DOCUMENTS

| | | |
|---|---|---|
| 2050786 | 3/1992 | Canada . |
| 327461 | 8/1989 | European Pat. Off. . |
| 327461 | 8/1989 | European Pat. Off. . |
| 474506 | 3/1992 | European Pat. Off. . |
| 519726 | 12/1992 | European Pat. Off. . |
| 0518448A1 | 12/1992 | European Pat. Off. . |
| 0559425A1 | 9/1993 | European Pat. Off. . |
| 584558 | 3/1994 | European Pat. Off. . |
| 2233619 | 3/1989 | Japan . |
| WO91/05045 | 4/1991 | WIPO . |
| WO92/21752 | 12/1992 | WIPO . |
| WO93/18061 | 9/1993 | WIPO . |

OTHER PUBLICATIONS

Lu et al.; 47 Cancer Research 4184–4188 (1987), "Protective Influence of Lactoferin on Mice Infected with FVC-P".
Bellamy et al., 1121 Biochim. Biophys. Acta 130–136(1992), "Identification of the Bactericidal Domain of Lactoferrin".
Milwood et al., "An Antiviral Effect of Human Lactoferrin", Abstracts, E-110, Am. Soc. Microbiol. (1989).
Jaroff, Time, May 23,1988 p. 56.
Sandshom et al. Drugs vol. 34 p. 372 (1987).
ASM News vol. 56 p. 368 (Jul. 1990).
Saunder's Dictionary p. 968 (1984).

*Primary Examiner*—Toni R. Scheiner
*Assistant Examiner*—Sheela J. Huff
*Attorney, Agent, or Firm*—Testa, Hurwitz & Thibeault, LLP

[57] ABSTRACT

This invention relates to inhibitors against viral infection and proliferation composed of peptides shown by below mentioned amino acid sequence (1) or (2).

```
              ┌──────────────────── S — S ──┐   (1)
A—Cys—Phe—Gln—Trp—Gln—Arg—Asn—Met—Arg—Lys—
                                              │
       Val—Arg—Gly—Pro—Pro—Val—Ser—Cys—B

┌──────────────────── S — S ──┐   (2)
C—Cys—Arg—Arg—Trp—Gln—Trp—Arg—Met—Lys—Lys—
                                              │
       Leu—Gly—Ala—Pro—Ser—Ile—Thr—Cys—D
```

The inhibitors against viral infection and proliferation of the present invention can suppress the infection and proliferation of influenza virus or cytomegalo virus, and are useful for the prevention and treatment of diseases caused by these viruses.

8 Claims, No Drawings

VIRAL INFECTION AND PROLIFERATION INHIBITORS

FIELD OF THE INVENTION

This invention relates to peptide inhibitors against viral infection and proliferation.

BACKGROUND OF THE INVENTION

Various efforts have been made to overcome diseases caused by viral infection. However, no effective treatments have been found to prevent and to cure diseases caused by some viruses such as recent serious world-wide epidemic of human immunodeficiency virus (HIV) and annual epidemic of influenza. Chemotherapeutic treatment with antiviral agents has been used to cope with these diseases caused by viral infections. At present, however, antiviral agents which are markedly effective against systemic infection are very few. Viruses proliferate within living cells and their major metabolic function for multiplication depends on living cells, that is, viruses use the growth ability of host human cells for proliferation after infection. Therefore, most chemical substances that suppress the growth of viruses also affect the host cells and exhibit toxicity. Antiviral agents have some essential problems to be solved due to characteristic features of viral infections in addition to their low selectivity between viruses and cells. Particularly, in patients with acute systemic viral infectious diseases symptoms are usually developed after the virus shows maximum growth in vivo, thus agents which prevent infection and/or suppress the proliferation have been required. One possible method for preventing the viral infection is a vaccination, but it often brings about allergic reactions and various side reactions, furthermore it is substantially ineffective against viral mutation.

The inventors found that iron-binding proteins such as lactoferrin (LF), transferrin and ovotransferrin inhibit the infection and growth of influenza virus and cytomegalo virus (CMV) and accomplished an invention (Japanese Un-examined Patent Publication No. 233619 (1990)). LF secreted in milk is known as an iron-binding protein which possesses antimicrobial activity. Human and bovine LFs have been investigated in detail and their total amino acid sequences have been determined (M. W. Rey et al., Nucleic Acids Res., 18, 5288 (1990) and P. E. Mead et al., ibid., 18, 7167 (1990)). Japanese Un-examined Patent Publication No. 233226 (1989) discloses an antiviral agent containing milk proteins such as LF as effective ingredients, explaining that LF is effective against viruses with and without envelope. Recently, the inventors confirmed the inhibitory effect of iron-binding proteins against infection and growth of HIV and accomplished an invention of HIV infection and growth inhibitor containing LF as an effective ingredient (Japanese Patent Application No. 220635 (1992)).

The characteristic features of iron-binding proteins such as LF against viral infection and proliferation have been gradually elucidated; their practical use as an antiviral agent has been expected. The practical use of these proteins as anti-infective and anti-proliferative agents requires ① no antigenicity when administered and ② availability in large quantity. Bovine LF and transferrin, and ovotransferrin of hen's egg can be supplied in large quantities but have drawbacks of antigenicity in human body. On the other hand, human LF has no antigenicity but is unresponsive for demands in large quantities.

Lactoferrin, an iron-binding protein, is well known in exhibiting antimicrobial activity, and antibacterial peptides with a part of the amino acid sequences of LF were recently isolated. EP-0474506 discloses two antibacterial peptides (SEQ. ID. NO.: 1) and (SEQ. ID. NO.: 2) derived from human and bovine LFs as shown below.

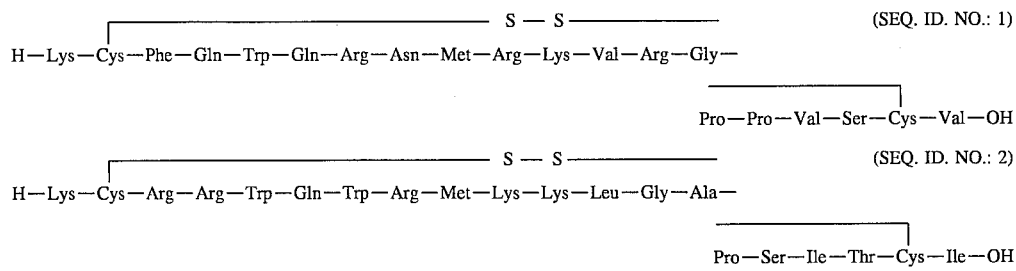

An antibacterial peptide having the amino acid sequence was named lactoferricin by Bellamy et al. (W. Bellamy et al., Biochim. Biophys. Acta, 1121, 130–136 (1992)). The antimicrobial activities to Gram negative bacteria, yeasts and fungi have been known, but no antiviral activity has been known.

The inventors investigated the isolation of a peptide having inhibitory activity against viral infection and proliferation from protease hydrolysate of LF which shows most potent inhibiting activity against viral proliferation among the iron-binding proteins disclosed in Japanese Unexamined Patent Publication No. 233619 (1990) to identify the active site of LF. Furthermore, the inventors chemically synthesized LF peptide fragments and studied their inhibitory activity against viral infection and proliferation. They found that a peptide fragment corresponding to 20–37 amino acid residues from N-terminal in human LF and a peptide fragment corresponding to 19–36 amino acid residues from N-terminal in bovine LF are active sites for the suppress of the viral infection and proliferation. Investigations on the synthetic peptides found that ① loop structure by S—S bond is not essential for the activity, which corresponds to 20 Cys-37 Cys in human LF and 19 Cys-36 Cys in bovine LF, respectively, ② acetylation of N-terminal of the loop peptides or an elongation of amino acid residue provides favorable effect to the activities, and ③ amidation of C-terminal of the loop peptides or the elongation of amino acid residue provides improved activities.

The antimicrobial activity of LF fragment including the peptide loop has been known (W. Bellamy et al., Biochim. Biophys. Acta 1121, 130–136 (1992) and D. Legrand et al., Biochemistry, 31, 9243–9251 (1992)); however, no inhibitory activity against viral infection and proliferation has been reported.

SUMMARY OF THE INVENTION

The object of the present invention is to provide inhibitors against viral infection and proliferation composed of an effective ingredient of peptide existing in the amino acid sequence of LF or a peptide derivative having the peptide sequence.

The effective ingredients against viral infection and proliferation provided by the present invention are expressed by the following amino acid sequences (SEQ. ID. NO.: 3) or (SEQ. ID. NO.: 4).

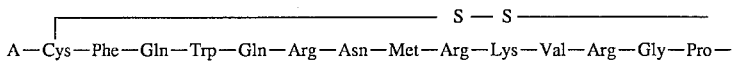

(wherein A represents free amino group, acetyl group or a peptide residue composed of two amino acids, B represents free carboxyl group, amide group or a peptide residue composed of five amino acids. The loop via S—S bond is not essential for the activity, and the S—S bond can be replaced by two reduced SH groups).

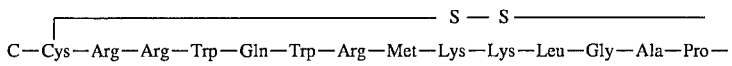

(wherein C represents free amino group, acetyl group or a peptide residue composed of two amino acids, D represents free carboxyl group, amide group or a peptide residue composed of five amino acids. The loop via S—S bond is not essential for the activity, and the S—S bond can be replaced by two reduced SH groups.

Thr-Lys-, Phe-Lys- and so forth may be exemplified as preferred peptide residues for A and C, whereas Ile-Lys-Arg-Asp-Ser- (SEQ. ID. NO.: 5), Val-Arg-Arg-Ala-Phe- (SEQ. ID. NO.: 6) and so forth for B and D.

Their pharmacologically acceptable salts such as hydrochloride, acetate and so forth may also be used.

DETAILED DESCRIPTION OF THE INVENTION AND PREFERRED EMBODIMENTS

Total amino acid sequences of human and bovine LFs are disclosed in M. W. Rey et al., Nucleic Acids Res., 18, 5288 (1990) and P. E. Mead et al., ibid., 18, 7167 (1990) and a sequence of Cys-Phe-Gln-Trp-Gln-Arg-Asn-Met-Arg-Lys-Val-Arg-Gly-Pro-Pro-Val-Ser-Cys in the above amino acid sequences includes 20–37 amino acids from N-terminal in the primary structure of human LF (SEQ. ID. NO.: 3) and a sequence of Cys-Arg-Arg-Trp-Gln-Trp-Arg-Met-Lys-Lys-Leu-Gly-Ala-Pro-Ser-Ile-Thr-Cys includes 19–36 amino acids from N-terminal in the primary structure of bovine LF (SEQ. ID. NO.: 4). These structures are essential to exhibit inhibitory activity against viral infection and proliferation as mentioned above. Hereinafter, the substance containing the amino acid sequence derived from LF and effective in inhibition of viral infection and proliferation is expressed by the amino acid sequence number of lactoferrin as shown by bovine LF (19–36). The peptides of the present invention can be obtained by any source including conventional chemical synthesis, isolation from protease hydrolyzed product of LF, gene recombination and so forth.

For Example, compounds shown by previously-described peptide sequences (3) and (4) can be obtained by treatment of human or bovine LF with a protease such as pepsin, followed by HPLC treatment as disclosed in EP-0474506.

In addition, the aimed peptide can be obtained by synthesis of linear peptides using a commercial peptide synthesizer, aetylation of N-terminal residue, and oxidation and cyclization in the presence of potassium ferricyanide to give the S—S bond formation in Cys-Cys.

These peptides or peptide derivatives are used to prepare pharmaceutical compositions singly or in combinations with excipient and stabilizers. The inhibitors against viral infection and proliferation of the present invention can be administered as oral, injection or suppository. Generally, the peptides and peptide derivatives are administered at daily doses of 6–30 g for adult patients. The inhibitors against viral infection and proliferation of the present invention are particularly and effectively administered between 24 hours before and one hour after the viral infection.

These peptides belong to parts of proteins conventionally used for food materials, thus there is no problem in safely. Particularly, peptide fragments derived from human LF have very low antigenicity and are preferable for practical use. The inhibitors against viral infection and proliferation of the present invention will be explained in detail by the following examples and experiments.

EXAMPLES

Example 1

Synthesis of human LF (20–37) (SEQ. ID. NO.: 3) and [20CysSH, 37CysSH]] human LF (20–37)

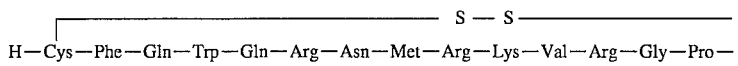

The linear protected peptide was synthesized at 0.25 mmol scale using 9-fluorenylmethyloxycarbonyl (Fmoc) group as a protecting group for the terminal amino group and p-hydroxymethylphenoxymethylpolystyrene (HMP) resin with a peptide synthesizer 431A (ABI Co., Ltd.). HMP resin and the protecting group were removed from the resultant 1,250 mg of the protected peptide—HMP resin complex simultaneously using trifluoroacetic acid (TFA) in the presence of phenol, 1,2-ethanedithiol and thioanisole. After TFA was removed by evaporation from the reaction mixture under vacuum, crude peptide was crystallized with ethyl ether. The crystals were dissolved in 5% acetic acid and lyophilized. The obtained 500 mg of crude linear peptide was subjected to HPLC [column: octadecyl 4PW (21.5×150 mm) (Tosoh Corp.), eluant: gradient elution with water-acetonitrile containing 0.1% TFA] to give 340 mg of purified linear peptide [20CysSH, 37CysSH] human LF (20–37).

Cyclization with S—S bond formation was performed with air oxidation in the presence of potassium ferricyanide and purified with HPLC as already described. The resultant 35 mg of the purified cyclic peptide showed purity of 93% by HPLC analysis. Absence of SH group was confirmed by Ellman's method; mass spectrometry confirmed monomer structure.

Example 2

Synthesis of human LF (18–48) (SEQ. ID. NO.: 7) and [20CysSH, 37CysSH]] human LF (18–42)

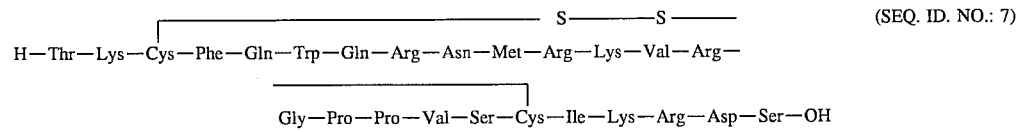
(SEQ. ID. NO.: 7)

The peptide shown above was synthesized by a similar manner with that of Example 1 using the peptide synthesizer 431A (ABI Co., Ltd.) and 420 mg of the linear peptide with a purity of 94% and 38 mg of the cyclic peptide with a purity of 96% were obtained.

Example 3

Synthesis of N-acetyl-human LF (20–37)-amide (Ac-human LF (20–37)-$NH_2$) (SEQ. ID. NO.: 3)

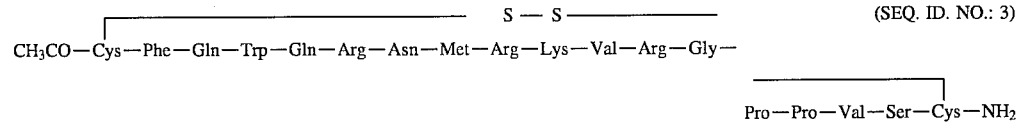
(SEQ. ID. NO.: 3)

The peptide shown above was synthesized at 0.25 mmol scale using tert-butyloxycarbonyl (t-Boc) group as a protective group for the terminal amino group using the peptide synthesizer 431A (ABI Co., Ltd.) and benzhydrylamine resin. After completion of the condensation reaction, t-Boc group at the N-terminal was removed and acetylated with acetic anhydride. Cleavage from the resin and removal of the protecting group were simultaneously performed by HF treatment. The reaction mixture was evaporated under vacuum to remove HF, and aimed crude Ac-human LF (20–37)-$NH_2$ was obtained. The resultant crude peptide was purified by a similar method with HPLC as that of Example 1. The obtained peptide was cyclized by the formation S—S bond with air oxidation in the presence of potassium ferricyanide and was further purified with HPLC to give 18 mg of the aimed cyclic peptide with a purity of 91%.

Example 4

Synthesis of bovine LF (19–36) (SEQ. ID. NO.: 4)

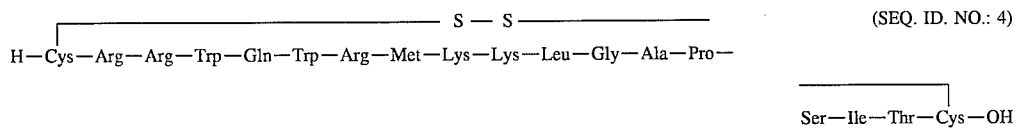
(SEQ. ID. NO.: 4)

The above mentioned peptide was synthesized by a similar manner with that of Example 1, and 40 mg of the cyclic peptide was obtained :with a purity of 94%.

Example 5

Synthesis of bovine LF (17–41) (SEQ. ID. NO.: 8) and [19CysSH, 36CysSH] bovine LF (17–41).

```
                    ┌──────────── S — S ────────────┐                    (SEQ. ID. NO.: 8)
H—Phe—Lys—Cys—Arg—Arg—Trp—Gln—Trp—Arg—Met—Lys—Lys—Leu—Gly—
                                                              ┐
                     Ala—Pro—Ser—Ile—Thr—Cys—Val—Arg—Arg—Ala—Phe—OH
```

The above mentioned peptide was synthesized by a similar manner with that of Example 1, and 380 mg of pure linear peptide [19CysSH, 36CysSH] bovine LF (17–41) with a purity of 91% and 28 mg of the cyclic peptide with a purity of 95%, respectively, were obtained.

Example 6
Synthesis of N-acetyl-bovine LF (19–36)-amide (Ac-bovine LF (19–36)-NH₂) (SEQ. ID. NO.: 4)

```
              ┌──────────── S — S ────────────┐                    (SEQ. ID. NO.: 4)
CH₃CO—Cys—Arg—Arg—Trp—Gln—Trp—Arg—Met—Lys—Lys—Leu—Gly—Ala—
                                                              ┐
                              Pro—Ser—Ile—Thr—Cys—NH₂
```

The peptide shown above was synthesized by a similar manner with that of Example 3, and 405 mg of the linear peptide with a purity of 92% and 19 mg of the cyclic peptide with a purity of 95%, respectively, were obtained.

Example 7
Preparation of the inhibitor compositions against viral infection and proliferation.

In the present Example, injection compositions were prepared using peptides obtained by the above mentioned Examples 1–6. These injection compositions can be used for intravenous administration.

| (1) Human LF (20–37) | 100 mg |
|---|---|
| Human serum albumin | 100 mg |

Above composition was dissolved in 0.01M phosphate buffered saline (PBS) at pH 7.0 and adjusted to make 20 ml in total. The resultant solution was sterilized and two ml each was divided in vials, lyophilized and sealed.

| (2) Human LF (18–42) | 100 mg |
|---|---|
| Tween 80 | 1 mg |
| Human serum albumin | 100 mg |

Above composition was dissolved in saline solution for injection and adjusted to make 20 ml in total. The resultant solution was sterilized and two ml each was divided in vials, lyophilized and sealed.

| (3) Ac-LF (20–37)-NH₂ | 100 mg |
|---|---|
| Tween 80 | 2 mg |
| Sorbitol | 4 g |

Above composition was dissolved in 0.01M PBS at pH 7.0 and adjusted to make 20 ml in total. The resultant solution was sterilized and two ml each was divided in vials, lyophilized and sealed.

| (4) Bovine LF (19–36) | 4 g |
|---|---|
| Tween 80 | 2 mg |
| Glycine | 2 g |

Above composition was dissolved in saline solution for injection and adjusted to make 20 ml in total. The resultant solution was sterilized and two ml each was divided in vials, lyophilized and sealed.

| (5) Bovine LF (17–41) | 2 g |
|---|---|

-continued

| Tween 80 | 1 mg |
|---|---|
| Sorbitol | 2 g |
| Glycine | 1 g |

Above composition was dissolved in saline solution for injection and adjusted to make 20 ml in total. The resultant solution was sterilized and two ml each was divided in vials, lyophilized and sealed.

| (6) Ac-bovine LF (19–36)-NH₂ | 4 g |
|---|---|
| Sorbitol | 4 g |
| Human serum albumin | 50 mg |

Above composition was dissolved in 0.01M PBS at pH 7.0 and adjusted to make 20 ml in total. The resultant solution was sterilized and two ml each was divided in vials, lyophilized and sealed.

By practicing the present invention, inhibitor compositions against viral infection and proliferation can be provided.

The effect of the inhibitor compositions of the present invention against viral infection and proliferation can be summarized as follows:

(1) Viral infection can be prevented. Increase in the number of infected cells with the virus in vivo can be suppressed for infected patients.

(2) The inhibitors are composed of effective ingredients which have been traditionally taken as foods, thus the administration can be performed without the risk of side effects.

(3) The inhibitors have low molecular weight and can be easily prepared in large scale by practical methods such as chemical synthesis, although manufacturing of iron-binding proteins such as LF free from antigenicity is impractical. Therefore, the inhibitors can be used widely for the prevention of viral infection and inhibition of proliferation without limitation to the treatment of specific patients.

The inhibitors against Vital infection and proliferation of the present invention are useful for the prevention and treatment of influenza and AIDS, and prevention of infection of cytomegalo virus during organ transplantation.

The effect of the present invention will be explained in detail by the following experiments.

Experiment 1
Determination of inhibitory activity against HIV infection and proliferation of a peptide derived from LF (Method) Cultured supernatant of MOLT-4/HTLV-IIIB cells, a HTLV-IIIB persistent infected strain of HIV, was used as a viral solution. The supernatant was kept at −80° C. Human T cell line MT-4 was used for the test. MT-4 was subcultured in RPMI 1640 medium containing 10% fetal calf serum (FCS). Sample, LF derived peptide, was dissolved in RPMI 1640 medium and one ml of the diluted solution at various concentrations was added to the cells. The inoculated MT-4 test sample was incubated for 60 minutes and infected with HIV at a concentration of moi (cells/infected virus)=0.01 and one ml of the cell solution adjusted at a cell density of $3 \times 10^5$ cells/ml was added. The cells were cultured for three days : and HIV infected cells were determined with an indirect fluorescence antibody method.

HIV infected cells were determined by the indirect fluorescence antibody method using HIV infected patient serum as a primary antibody. More than 500 cells were observed with a fluorescence microscope and the ratio of stained cells were calculated. HIV infected MT-4 cells cultured without addition of the sample was used as a positive control and cells without addition of viral solution was cultured to make a negative control group.

(Results) The results of experiment indicating the ratios of stained cells are shown in Table 1. All peptides showed the same activity levels with that of LF. Positive control HIV infected MT-4 cells showed stained rate of 26.0% and MT-4 cells without addition of HIV showed the corresponding rate of 0%.

TABLE 1

Inhibitory effect of lactoferrin and lactoferrin derived peptide against HIV infection and proliferation

| | Concentrations added (μg/ml) | | | | |
|---|---|---|---|---|---|
| Sample | 1,000 | 500 | 250 | 125 | 63 |
| Human LF | 3.1 | 5.8 | 7.3 | 8.6 | 17 |
| Human LF (20–37) | 4.4 | 6.0 | 8.9 | 10.9 | 19 |
| Human LF (18–42) [20CysSH, 37CysSH] | 1.1 | 2.9 | 6.7 | 8.8 | 17 |
| Human LF (18–42) | 1.4 | 3.1 | 6.2 | 8.5 | 17 |
| Ac-human LF (20–37)-NH$_2$ | 3.9 | 4.5 | 7.7 | 9.8 | 18 |
| Bovine LF | 3.6 | 4.8 | 6.2 | 8.0 | 18 |
| Bovine LF (19–36) | 4.8 | 5.9 | 8.9 | 9.9 | 20 |
| Bovine LF (17–41) [19 CysSH, 36 CysSH] | 1.0 | 2.7 | 5.9 | 7.9 | 17 |
| Bovine LF (17–41) | 1:2 | 2.9 | 6.4 | 8.3 | 19 |
| Ac-bovine LF (19–36)-NH$_2$ | 3.6 | 5.0 | 6.1 | 8.8 | 17 | unit %

Experiment 2
Determination of inhibitory activity of peptide derived from LF against influenza virus infection and proliferation (Method) The inhibitory activity of peptide derived from LF against influenza viral infection and proliferation was determined by embryonated hen's egg culture method according to "General Viral Experiments" Ed. by Fellow Membership of The National Institute of Health, p. 113–129, Maruzen Co., Ltd. (1973). Human LF, bovine LF and peptides prepared by Examples 1–6 were dissolved in saline solution to give a concentration of one mg/ml, filtered and sterilized. Fifty embryonated eggs were divided in ten groups each containing five eggs at day 10. Control group was given saline solution and the other groups were inoculated with 100 μl each of the test solution in allantoic cavity. After three hours, 100 μl each of influenza virus A/PR/8/34 solution was inoculated in the allantoic cavity of embryonated eggs. The amount of virus used here was that of positive to hemagglutination (HA) reaction in cultured fluid prepared by inoculation in allantoic cavity, collecting of allantoic fluid and 64-fold dilution of the fluid. After two days, the eggs were placed overnight in a refrigerator, then the allantoic fluid was collected. The obtained fluid was serially diluted with saline solution, added with stabilized chick erythrocyte (Takeda Chemical Ind. Ltd.) and HA reaction was determined.

(Results) The results of experiment are shown in Table 2. The inhibitory rate of infection and proliferation of influenza virus was calculated from the amount of virus of each group in comparison to that of the control group solely inoculated with the virus and made 100%. The numerals indicate the average value of each group. All peptides showed similar activity levels with that of LF.

TABLE 2

Inhibitory effect of lactoferrin and lactoferrin derived peptide against influenza virus infection and proliferation

| Sample | Inhibitory rate (%) |
|---|---|
| Human LF | 87.5 |
| Human LF (20–37) | 75.0 |
| Human LF (18–42) | 96.9 |
| [20 CysSH, 37 CysSH] Human LF (18–42) | 96.0 |
| Ac-human LF (20–37)-NH$_2$ | 93.7 |
| Bovine LF | 87.5 |
| Bovine LF (19–36) | 50.0 |
| Bovine LF (17–41) | 93.7 |
| [19 CysSH, 36 CysSH] Bovine LF (17–41) | 92.0 |
| Ac-bovine LF (19–36)-NH$_2$ | 87.5 |

Experiment 3
Determination of inhibitory activity of peptide derived from LF against CMV infection and proliferation (Method) LF derived peptide was dissolved in 2% serum added MEM medium to give five mg/ml solution, filtered and sterilized to make a stock solution. The stock solution was diluted with 2% serum added MEM medium on use. Samples containing human embryo lung fibroblast cells (HELF cells) were suspended in 2% serum added MEM medium and incubated for 10 minutes. The cells were collected by centrifugation, washed twice with 2% serum added MEM medium and suspended in 2% serum added MEM medium. Human cytomegalo virus [Human CMV (Tanaka strain)] was added, incubated for 24 hrs., fluorescence stained with human CMV positive serum and the adsorption rate of human CMV to the cells was determined.

(Results) The results are shown in Tables 3 and 4. The results are judged from the numbers of fluorescent stained cells per one cover slip. All samples showed similar activity levels with that of LF.

TABLE 3

Inhibitory effect of LF derived peptide against human CMV infection and proliferation

| Sample | Inhibitory rate of human CMV infection (%) |
|---|---|
| Human LF | 94.8 |
| Human LF (20–37) | 94.0 |
| Human LF (18–42) | 95.7 |
| [20 CysSH, 37 CysSH] Human LF (18–42) | 100.0 |

TABLE 3-continued

Inhibitory effect of LF derived peptide against human CMV infection and proliferation

| Sample | Inhibitory rate of human CMV infection (%) |
|---|---|
| Ac-human LF (20–37)-NH$_2$ | 96.1 |
| Bovine LF | 95.7 |
| Bovine LF (19–36) | 93.9 |
| Bovine LF (17–41) | 95.7 |
| [19 CysSH, 36 CysSH] Bovine LF (17–41) | 100.0 |
| Ac-bovine LF (19–36)-NH$_2$ | 96.5 |

TABLE 4

Inhibitory effect of human LF (18–42) against human CMV infection and proliferation

| Concentration (mg/ml) | Inhibitory rate (%) |
|---|---|
| 0.04 | 14.7 |
| 0.1 | 34.9 |
| 0.2 | 45.0 |
| 0.4 | 51.9 |
| 1.0 | 86.0 |
| 2.0 | 96.1 |

Experiment 4
Determination of in vivo inhibitory activity against CMV infection (Method) Male Balbc/AJcl mice, 4-week-old (10 in one group) were used. The sample was dissolved in phosphate buffer saline solution (PBS) and intraperitoneally administered to mice. After 24 hrs., 1×10$^6$ PFU of mouse cytomegalo virus (mouse CMV) was intraperitoneally administered, and survival rate of mice after 10 days was observed for the evaluation of inhibitory effect against infection.

(Results) Table 5 shows the results. The peptides of the present invention exhibited inhibitory effect against mouse CMV infection at doses of 0.1 g/kg of body weight or over.

TABLE 5

In vivo inhibitory effect against mouse CMV infection

| Sample | Dose (g/kg of body weight) | Survival rate (%) |
|---|---|---|
| Positive control | — | 100 |
| Negative control | — | 0 |
| Human LF (18–42) | 0.02 | 20 |
|  | 0.05 | 50 |
|  | 0.10 | 100 |
|  | 0.50 | 100 |
| Bovine LF (17–41) | 0.02 | 30 |
|  | 0.05 | 60 |
|  | 0.10 | 100 |
|  | 0.50 | 100 |

Experiment 5
Infection protective test and determination of appropriate timing of administration against cytomegalovirus infection (Method) Male Balbc/AJcl mice, 4-week-old (10 in one group) were used. The sample was dissolved in phosphate buffer saline solution (PBS) and intraperitoneally administered to mice. After 24 hrs., 1×10$^6$ PFU of mouse cytomegalo virus (mouse CMV) was intraperitoneally administered, and survival rate of mice after 10 days was observed for the evaluation of inhibitory effect against infection. Timing of administrations of the sample was made 48, 24, six and one hr. before, immediately after, one and six hrs. after the administration.

(Results) The results are shown in Table 6. The most appropriate timing of administration of the peptide of present invention was between 24 hrs. before and one hr. after the infection.

TABLE 6

Infection protective test against mouse CMV by the time of administration

| Sample | Dose (g/kg of body weight) | Time of administration (hrs.)* | Survival rate (%) |
|---|---|---|---|
| Positive control | — | — | 100 |
| Negative control | — | — | 0 |
| Human LF (18–42) | 0.10 | –48 | 60 |
|  | 0.10 | –24 | 100 |
|  | 0.10 | –6 | 100 |
|  | 0.10 | –1 | 100 |
|  | 0.10 | 0 | 100 |
|  | 0.10 | +1 | 100 |
|  | 0.10 | +6 | 60 |

*: Time (hrs.) based on the start of administration

---

We claim:

1. A composition for diminishing viral infection and proliferation comprising:

a peptide having the amino acid sequence A-Cys-Phe-Gln-Trp-Gln-Arg-Asn-Met-Arg-Lys-Val-Arg-Gly-Pro-Pro-Val-Ser-Cys-B (Seq. ID No. 3) in an amount sufficient to diminish viral infection and proliferation, wherein A- is a free amino group, an acetyl group or a dipeptide and -B is a pentapeptide having the amino acid sequence Val-Arg-Arg-Ala-Phe (Seq. ID No. 6); and a pharmaceutically-acceptable carrier.

2. The composition of claim 1 wherein the dipeptide has the amino acid sequence Thr-Lys.

3. The composition of claim 1 wherein the dipeptide has the amino acid sequence Phe-Lys.

4. The composition of claim 1 wherein the Cys residues are linked by a disulfide bond.

5. A composition for diminishing viral infection and proliferation comprising:

a peptide having the amino acid sequence C-Cys-Arg-Arg-Trp-Gln-Trp-Arg-Met-Lys-Lys-Gly-Ala-Pro-Ser-Ile-Thr-Cys-D (Seq. ID No. 4) in an amount sufficient to diminish viral infection and proliferation, wherein C- is a free amino group, an acetyl group or a dipeptide and -D is a pentapeptide having the amino acid sequence Ile-Lys-Arg-Asp-Ser (Seq. ID No. 5); and a pharmaceutically-acceptable carrier.

6. The composition of claim 5 wherein the dipeptide has the amino acid sequence Phe-Lys.

7. The composition of claim 5 wherein the dipeptide has the amino acid sequence Thr-Lys.

8. The composition of claim 5 wherein the Cys residues are linked by a disulfide bond.

* * * * *

UNITED STATES PATENT AND TRADEMARK OFFICE
CERTIFICATE OF CORRECTION

PATENT NO. : 5,565,425
DATED : October 15, 1996
INVENTOR(S) : N. Yamamoto, H. Nakashima, W. Motsuchi, S. Tanaka, S. Dosako, Y. Kawasaki, and T. Uchida It is certified that error appears in the above-indentified patent and that said Letters Patent is hereby corrected as shown below:

In column 18, line 22 (line 4 of claim 5), please insert --Leu--- between "Lys-" and "Gly" so as to read "Lys-Leu-Gly".

Signed and Sealed this

Thirteenth Day of May, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..20
    ( D ) OTHER INFORMATION: /note="ANTIBACTERIAL PEPTIDE DERIVED FROM HUMAN LACTOFERRIN"

( x i ) SEQUENCE DESCRIPTION: SEQ ID NO:1:

Lys Cys Phe Gln Trp Gln Arg Asn Met Arg Lys Val Arg Gly Pro Pro
1               5                   10                  15
Val Ser Cys Val
            20

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..20
        ( D ) OTHER INFORMATION: /note="ANTIBACTERIAL PEPTIDE DERIVED FROM BOVINE LACTOFERRIN"

( x i ) SEQUENCE DESCRIPTION: SEQ ID NO:2:

Lys Cys Arg Arg Trp Gln Trp Arg Met Lys Lys Leu Gly Ala Pro Ser
1               5                   10                  15
Ile Thr Cys Ile
            20

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..18
        ( D ) OTHER INFORMATION: /note="HUMAN LACTOFERRIN PEPTIDE ( 2 0 - 3 7 )"

( x i ) SEQUENCE DESCRIPTION: SEQ ID NO:3:

Cys Phe Gln Trp Gln Arg Asn Met Arg Lys Val Arg Gly Pro Pro Val
1               5                   10                  15
Ser Cys ( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..18
        ( D ) OTHER INFORMATION: /note="BOVINE LACTOFERRIN PEPTIDE ( 1 9 - 3 6 )"

( x i ) SEQUENCE DESCRIPTION: SEQ ID NO:4:

Cys Arg Arg Trp Gln Trp Arg Met Lys Lys Leu Gly Ala Pro Ser Ile
1               5                   10                  15

Thr Cys ( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note="PEPTIDE B"

( x i ) SEQUENCE DESCRIPTION: SEQ ID NO:5:

Ile Lys Arg Asp Ser
1               5

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note="PEPTIDE D"

( x i ) SEQUENCE DESCRIPTION: SEQ ID NO:6:

Val Arg Arg Ala Phe
1               5

( 2 ) INFORMATION FOR SEQ ID NO:7:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..25
        ( D ) OTHER INFORMATION: /note="HUMAN LACTOFERRIN PEPTIDE
            ( 1 8 - 4 8 )"

( x i ) SEQUENCE DESCRIPTION: SEQ ID NO:7:

Thr Lys Cys Phe Gln Trp Gln Arg Asn Met Arg Lys Val Arg Gly Pro
1               5                   10                  15

Pro Val Ser Cys Ile Lys Arg Asp Ser
                20                  25

( 2 ) INFORMATION FOR SEQ ID NO:8:

( i ) SEQUENCE CHARACTERISTICS:
        ( A ) LENGTH: 25 amino acids
        ( B ) TYPE: amino acid ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..25
        ( D ) OTHER INFORMATION: /note="BOVINE LACTOFERRIN PEPTIDE
            ( 1 7 - 4 1 )"

( x i ) SEQUENCE DESCRIPTION: SEQ ID NO:8:

Phe Lys Cys Arg Arg Trp Gln Trp Arg Met Lys Lys Leu Gly Ala Pro
    1               5                   10                  15

Ser Ile Thr Cys Val Arg Arg Ala Phe
                    20                  25